Figure 1:
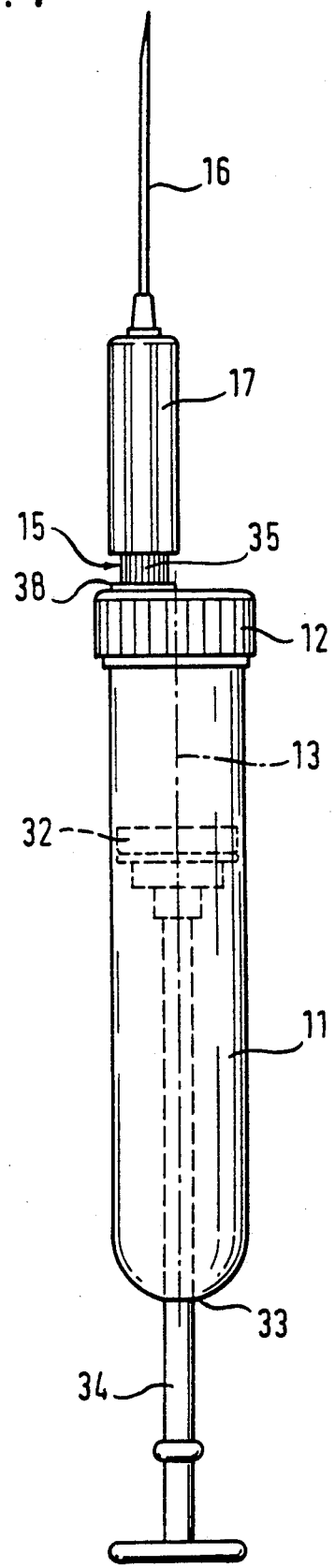

United States Patent [19]

Sarstedt

[11] Patent Number: 5,074,312
[45] Date of Patent: Dec. 24, 1991

[54] BLOOD EXTRACTION DEVICE WITH PENETRABLE PLUG ADAPTER

[75] Inventor: Walter Sarstedt, Nümbrecht, Fed. Rep. of Germany

[73] Assignee: Walter Sarstedt Gerate und Verbrauchs-material fur Medizin und Wissenschaft, Fed. Rep. of Germany

[21] Appl. No.: 513,523

[22] Filed: Apr. 19, 1990

[30] Foreign Application Priority Data

Apr. 21, 1989 [DE] Fed. Rep. of Germany ....... 3913197

[51] Int. Cl.⁵ .............................................. A61B 5/00
[52] U.S. Cl. .................................. 128/764; 128/765; 604/240
[58] Field of Search ..................... 128/763, 764, 765; 604/187, 200, 201, 240, 243

[56] References Cited

U.S. PATENT DOCUMENTS

| | | | |
|---|---|---|---|
| 4,192,320 | 3/1980 | Megahed | 128/764 |
| 4,378,812 | 4/1983 | Sarstedt | 128/765 |
| 4,449,539 | 5/1984 | Sarstedt | 128/764 |
| 4,576,595 | 3/1986 | Aas et al. | 128/763 X |

Primary Examiner—Max Hindenberg
Assistant Examiner—James M. Boler
Attorney, Agent, or Firm—Townsend and Townsend

[57] ABSTRACT

A blood extraction device comprises an evacuatable extraction tube (11) which is open at one end and onto which a closure cap (12) can be detachably fitted which carries a cannula cone (14) which projects forwardly parallel to the tube axis (13) and extends concentrically into a cylindrical extenion (15) having a smaller diameter than the extraction tube (11) and constructed as rearwardly open tube and which consists of a rearwardly open stiff sleeve (20) closed at the front except for a needle passage opening (19) and a counter piece (21) adapted to be fitted sealingly onto the cannular cone (14) and having a passage (22). Onto the extension (15) a guide sleeve (17) can be pushd axially from the front, said sleeve being complementary thereto open at the rear and at the front carrying a cannula (16) sharpened on both sides, the cannula end (16a) extending into the interior of the guide sleeve (17) piercing an elastic plate (18) arranged near the needle passage opening (19), in axial alignment therewith and representing a part of the extension (15) and thus establishing a flow connection between the interior of the cannula (16) and the interior of the cannula cone (14). According to the invention the counter piece is a soft-elastic plug (21) which is inserted into the stiff sleeve (20) and has a passage (22) which is open towards the screw cap (12), is adapted to be brought into a clamping fit with the cannula cone (14) holding the extension (15) firmly but releasably on the screw cap (12) and which is sealed at the front by the eleastic plate (18) which consists of one piece with the plug (21).

20 Claims, 4 Drawing Sheets

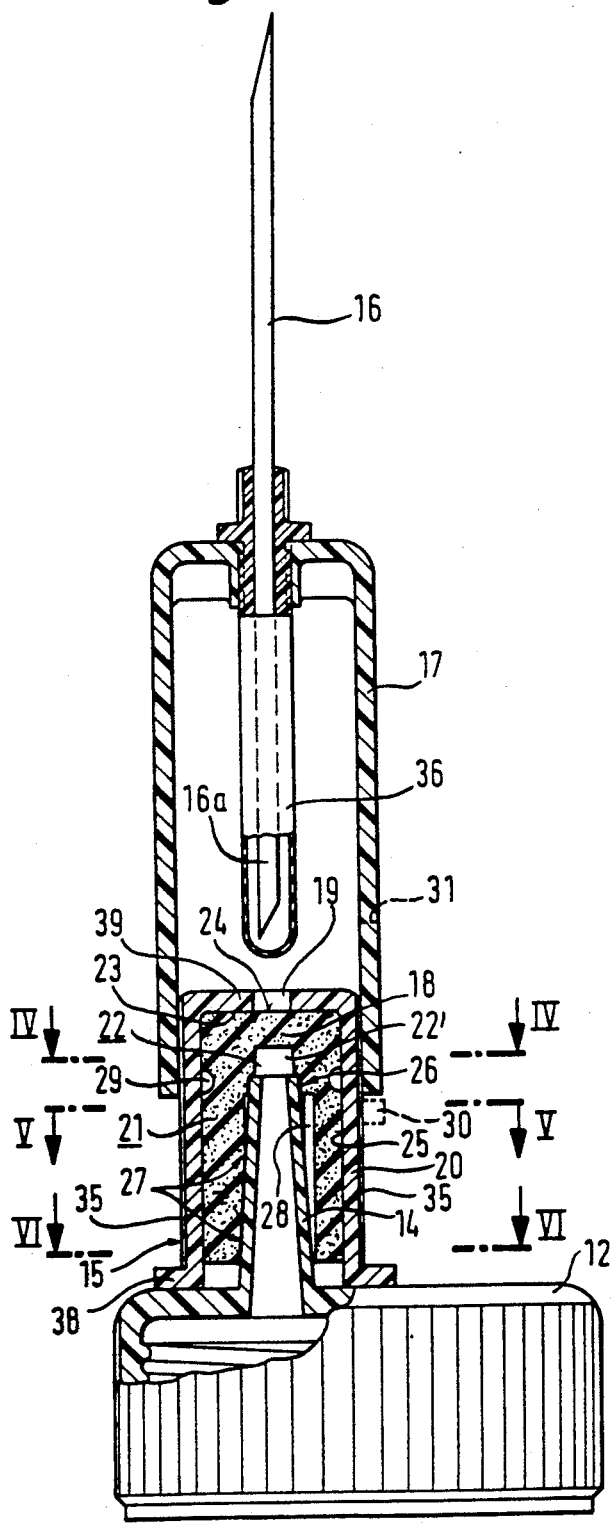
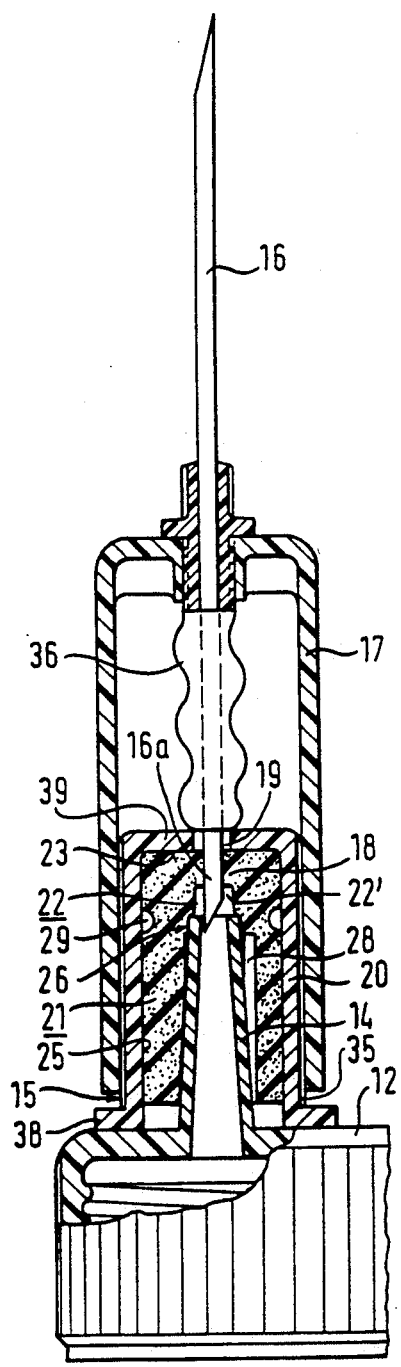

BLOOD EXTRACTION DEVICE WITH PENETRABLE PLUG ADAPTER

The invention relates to a blood extraction device comprising an evacuated or evacuatable extraction tube which is open at one end and onto which a closure cap can be detachably fitted which carries a cannula cone which projects forwardly parallel to the tube axis and extends preferably concentrically into an at least substantially cylindrical extension which has a smaller diameter than the extraction tube, is constructed substantially as rearwardly open tube and consists of a rearwardly open stiff sleeve closed at the front except for a needle passage opening and a counter piece adapted to be fitted sealingly onto the cannula cone and having a passage, and onto which a guide sleeve can be pushed axially from the front, said sleeve being substantially complementary thereto, open at the rear and carrying at the front preferably likewise concentrically a cannula sharpened on both sides, the cannula end extending into the interior of the guide sleeve piercing an elastic plate arranged near the needle passage opening, in axial alignment therewith and representing a part of the extension and thus establishing a flow connection between the interior of the cannula and the interior of the cannula cone.

Figure 5:
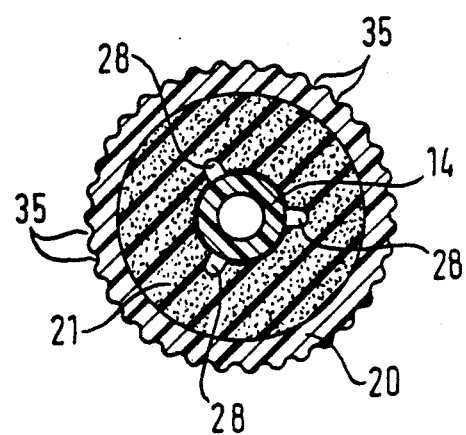
Figure 6:
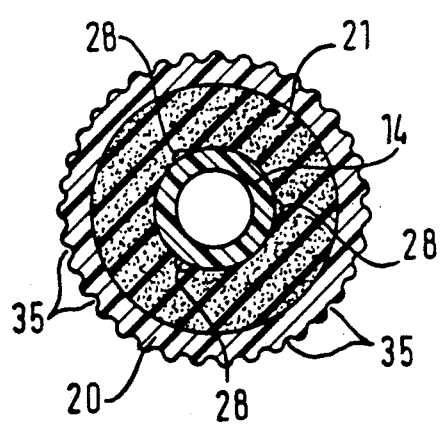

Such a blood extraction device is known from FIGS. 5 and 6 of DE-C2 29 48 653. The extension used therein is an adaptor intended to permit the use of the guide sleeve carrying the double-ended cannula also in conjunction with a conventional cannula cone.

It is however not expedient to use this known adaptor as extension permanently arranged on the cannula cone which only in exceptional cases, where a normal cannula is to be employed instead of the guide sleeve, is withdrawn from the cannula cone to make room for the receiving cone provided at the rear end of the normal cannula. For the known adaptor, in order to fulfill this purpose, would have to be pressed so firmly onto the cannula cone of the screw cap that in normal use employing the cylindrical guide sleeve no unintentional detaching of the adaptor from the screw cap can occur. As a result, however, the known adaptor would be fitted on the cannula cone so firmly that release by hand would be impossible or possible only under great difficulty. The firm pressing of the adaptor consisting of stiff plastic material onto the cannula cone also involves the danger that the surface of the cannula cone can become deformed or damaged so that it can no longer fulfill in the necessary manner its function as sealing surface with respect to the receiving cone of a normal cannula.

It is also already known to form the cylindrical extension as cylindrical rubber part which comprises a bore adpated to the cannula cone and is placed clampingly on said cannula cone. Although due to the soft-elastic properties of rubber a certain sealing reception of the cannula cone takes place here, on placing the rubber extension onto the cannula cone the latter is not only undesirably widened, resulting in deformation of the outer surface provided for the guide sleeve, but in addition the clamping force necessary for holding the extension on the cannula cone is restricted in undesirable manner because of the rubber-elastic properties of the extension.

The objective of the present invention resides in providing a blood extraction device of the type set forth at the beginning in which the extension detachably arranged on the screw cap in the intended use with guide sleeve is arranged adequately firmly and tightly on the cannula cone but nevertheless can be withdrawn from the cannula cone by hand by applying release forces which are not too small in order to enable a normal cannula with conical receiving space at the rear end to be used instead of the guide sleeve having a cannula sharpened at both sides; the following requirements are to be simultaneously fulfillled:

a) Absolute seal between cannula cone and extension in the region of the transition from the cannula end to the entrance end of the cannula cone;

b) a firm clamping fit of the extension on the cannula cone which can be released only by relatively large forces still exertable however by hand;

c) keeping stiff mounting surfaces deforming and/or damaging the surface of the cannula cone away from said surface of said cone and d) avoiding widening of the outer surface of the extension due to the press connection to the cannula cone.

To solve this problem the invention provides that the counter piece is a soft-elastic plug which is inserted into the stiff sleeve and preferably consists of rubber and which has a passage which is open towards the screw cap, is adapted to be brought into a clamping fit with the cannula cone holding the extension firmly but releasably on the screw cap and which is sealed at the front by the elastic plate. Preferably, the elastic plate consists of one piece with the plug.

The idea underlying the invention is thus to be seen in that the extension is stiff on the outside and soft-elastic on the inside so that by the pressing of the extension onto the cannula cone although by corresponding deformation of the soft-elastic material the necessary sealing and clamping forces for the holding are obtained no widening of the extension is however involved because the plug is defined as regards its outer form by the stiff sleeve and firmly held. In this manner, substantially greater clamping forces are also obtained for holding the extension on the cannula cone because on fitting the passage formed with smaller cross-section than the cannula cone onto the latter the soft-elastic material of the plug is merely compressed in radial direction but not radially widened.

Since solely soft-elastic material is in engagement with the surface of the stiff cannula cone there is no danger of a deformation and/or damage of the surface of the cannula cone so that said surface completely retains its perfect state for occasionally accommodating a normal cannula cone.

In spite of the firm fit and the good sealing the extension according to the invention can be released by applying relatively high forces by hand by combining a turning movement with an axial withdrawal movement.

Since the plug according to the invention is formed from soft-elastic material it is also suitable for performing the function of the piercable and then self-closing elastic plate. In this embodiment the soft-elastic plug preferably consisting of rubber according to the invention fulfills several functions, such as the following:

it forms the piercable and then again self-sealing elastic plate;

it serves for sealing in particular the front end of the cannula cone;

it serves in cooperation with the stiff sleeve to apply the clamping force for holding the extension on the cannula cone.

It is particularly advantageous for the front end face of the elastic plate to be flush with the front end face of the plug. In this manner the plug preferably formed outside as a cylindrical block with plane end faces can be inserted fittingly up to the plane end wall of the sleeve comprising the needle passage opening on the inside, the elastic plate thereby being forwardly supported on withdrawal of the needle of the guide sleeve.

It may be advantageous for the plug to have a cylindrical outer surface and the sleeve to have a cylindrical inner peripheral surface.

A further advantageous development of the invention is characterized in that the plug, at least when the extension is fitted, is pressed with its outer surface against the inner peripheral surface of the sleeve. In this manner, by the radial holding a particularly strong application force on the cannula cone is achieved.

For the assembly and later use it is expedient for the plug without inserted cannula cone to fit with easy self-retaining frictional fit in the sleeve. The plug should thus not be able to drop out of the stiff extension sleeve on its own; it suffices when the clamping forces necessary for the sealing and holding on the cannula cone are achieved only on fitting the extension to the cannula cone.

A particularly advantageous practical embodiment is so configured that the passage is surrounded in the region of the tip of the cannula cone sealingly by the material of the plug so that a sealing region is present there.

In this embodiment it is further advantageous if the passage comprises behind the sealing region at least one axially extending vent groove and in said region is detachably connected in firm clamping fit to the cannula cone.

Thus, according to the invention a clear distinction is made between a region serving primarily for the sealing at the front end of the cannula cone and a rear clamping region serving primarily for firmly holding the extension on the cannula cone. In this manner the pronounced deformations of the plug resulting from strong clamping are kept away from an actual sealing region where excessive clamping forces are less important than uniform bearing of regions of the plug which are as undeformed as possible on the periphery of the cannula cone. Where pronounced elastic deformations take place a certain sticking of the soft-elastic material in assembly and resulting leakage points must always be expected.

In accordance with the invention in the region behind the sealing region axially extending vent passages or grooves are even deliberatly provided so that air inclusions here do not lead to undesired deformations or undefined engagement surfaces. In particular, in this manner air inclusions are prevented from propagating themselves into the sealing region and leading there to leak points. In this manner, entraining of liquid on withdrawing the extension from the cannula cone is also avoided.

The underlying idea of the aforementioned embodiment is thus to be seen in that in the front region of the cannula cone only a slightly clamping but therefore particularly uniform and sealing engagement of the material of the plug on the periphery of the cannula cone is ensured whilst therebehind the sealing in the axial direction is deliberately avoided and instead a greatly increased clamping force is applied.

Since a sealing is important only in the front region of the cannula cone the invention expediently provides that the sealing region extends over 5 to 20%, in particular about 10%, of the length of the portion of the passage in contact with the cannula cone.

A particularly clear separation of sealing and clamping regions can be achieved in that the passage comprises behind the elastic plate a short portion of circular cross-section which has a slightly smaller diameter than the front end region of the cannula cone likewise having a circular cross-section and into which the front end region of the cannula cone sealingly engages.

In particular, it is to be provided that the cross-section of the passage widens behind the sealing region but only to such a slight extent that due to the conical widening of the cannula cone a clamping region is still present.

Finally, it is expedient for the cross-section of the passage to widen abruptly behind the sealing region and then remain unchanged up to the rear end of the passage.

Due to the preferably abrupt cross-sectional change of the passage at the rear end of the sealing region the action of clamping stresses is effectively avoided in the sealing region particularly sensitive thereto.

Due to the conically widening configuration of the cannula cone, in this manner occurrence of clamping stresses in the front region of the cannula cone is also avoided. Due to the widening of the cannula cone to the rear the clamping stresses then do not occur until a pronounced distance from the sealing region so that sealing and clamping region are separated from each other by a considerable axial distance. A preferred practical embodiment is characterized in that in the clamping region at least one, preferably however a plurality of circumferentially distributed axial vent grooves are provided of such a depth that even when the extension is fitted on the cannula cone an air passage still remains at the rear end.

A further advantageous embodiment is defined in that with a square cross-section of the passage in the clamping region the axial vent grooves are automatically realized by the corners of the square cross-section. The regions between the ends serve as clamping jaws pressing against the cannula cone from four sides.

Keeping excessive clamping stresses away in the region of the front end of the cannula cone is further enhanced in that in the region of the front end of the cannula cone in the outer surface of the plug a peripheral groove is disposed which permits a gentle and uniform resilient widening of the passage on insertion of the tip of the cannula cone in said region and thus a uniform sealing engagement of the plug in the sealing region on the periphery of the cannula cone.

A constructionally particularly compact arrangement is characterized in that the tip of the cannula cone extends at least approximately up to the rear face of the elastic plate. The tip can even contact the elastic plate from behind, thereby achieving a seal in the region of the end face of the cannula cone as well.

A further step promoting a compact structure is one in which the peripheral groove starts immediately behind the region of the elastic plate.

It is particularly advantageous for the sleeve on the extension and the guide sleeve to have bayonet fastening means, enabling fastening of the guide sleeve to the extension in accordance with DE-C2 30 49 503. In this embodiment there is the further advantage that by arranging the guide sleeve on the extension with the minimum possible friction and possibly even with play attachment of the guide sleeve to the extension and removal of the guide sleeve from said extension is possible without any problems and without any danger of the extension being pulled off the cannula cone. Due to the combination of a soft-elastic plug with a stiff sleeve deformation of the outer periphery of the extension is avoided, which could otherwise lead to intensified clamping of the guide sleeve on the extension.

Figure 4:
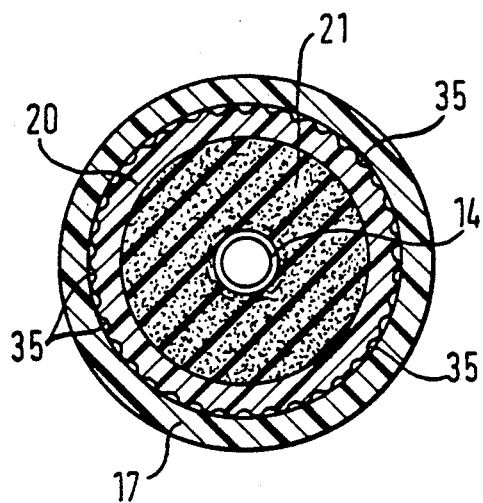
Figure 7:
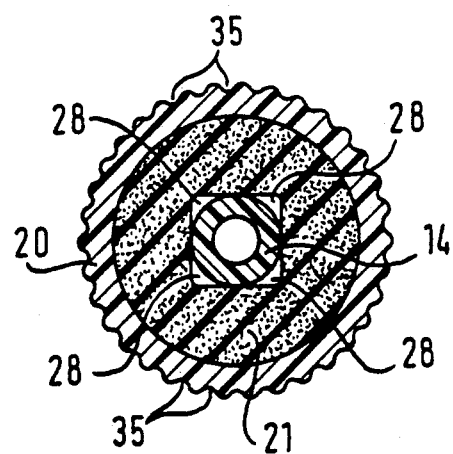
Figure 8:
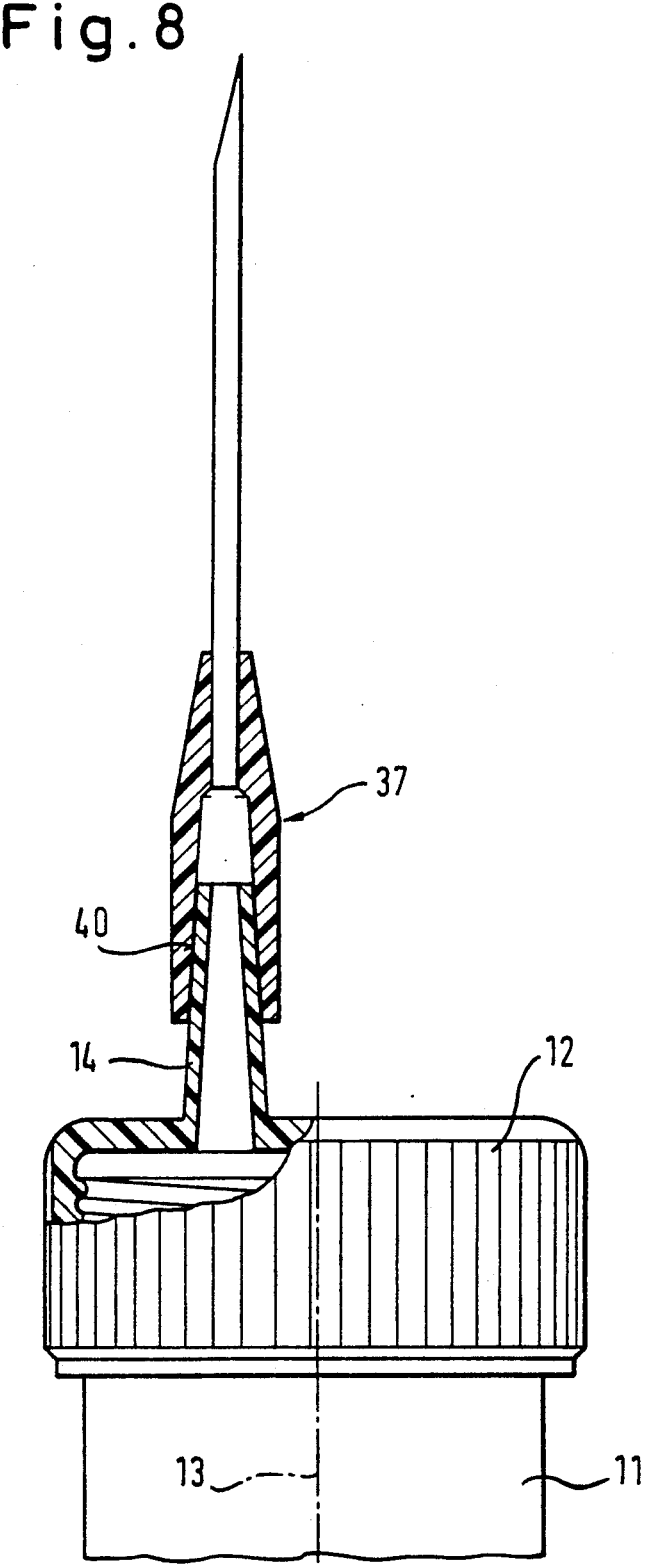

The invention will be described hereinafter by way of example with the aid of the drawings, wherein:

FIG. 1 is a side view of a blood extraction device according to the invention,

FIG. 2 is an enlarged partially sectioned side view of the front end of the blood extraction device according to FIG. 1, the guide sleeve 17 first being shown only partially pushed onto the extension 15, FIG. 3 is a partially sectioned side view analogous to FIG. 2 but with the guide sleeve 17 pushed further onto the extension 15, FIG. 4 is a section along the line IV—IV of FIG. 2, FIG. 5 is a section along the line V—V of FIG. 2, FIG. 6 is a section along the line VI—VI of FIG. 2, FIG. 7 is a section along the line V—V of FIG. 2 of a somewhat modified embodiment and FIG. 8 is a partially sectioned view analogous to FIG. 1 but with a normal cannula 37 fitted onto the cannula cone 14 instead of the extension 15.

In accordance with FIG. 1 in the extraction tube 11 of a blood extraction device a piston 32 is arranged for axial displacement and can be axially displaced by means of a piston rod 34 led through the rear end 33 of the extraction tube 11. The front end of the extraction tube 11 is open and is provided with an external thread onto which a closure cap 12 provided with an internal thread is screwed.

In accordance with FIG. 2 a cannula cone 14 extends from the front end of the closure cap 12 eccentrically to the axis 13 of the extraction tube 11 into an extension 15 which consists of an inner soft-elastic plug 21 of for example rubber and a stiff sleeve 20 of for example plastic surrounding said plug. A guide sleeve 17 complementary to said extension is adapted to be pushed onto the extension 15 provided externally with axial vent grooves 35 and in the front end wall of said guide sleeve a cannula 16 sharpened on both sides is arranged, the rear portion 16a of which is sealingly surrounded by a resilient hose 36. In FIG. 2 the guide sleeve 17 is shown in a position only slightly pushed onto the extension 15 whilst FIG. 3 shows the guide sleeve 17 in a state already almost completely fitted to the extension 15.

According to FIGS. 2 and 4 to 6 the sleeve 20 consisting of stiff or rigid plastic material has substantially cylindrical cross-section. It is relatively thin-walled and at its rear end has a radially outwardly projecting peripheral flange 38 by which the engagement area on the front end face of the closure cap 12 is enlarged. At the front end the sleeve 15 is provided with a radially inwardly projecting end flange 39 and radially within the latter a circular needle passage opening 19 is provided which is aligned with the rear portion 16a of the cannula 16 and has a somewhat greater diameter than the latter. The diameter of the needle passage opening 19 is however appreciably smaller than that of the hose 36 so that the latter, when the guide sleeve 17 is pushed onto the extension 15, can bear on the end flange 39 round the needle passage opening 19 as illustrated in FIG. 3.

The soft-elastic plug 21 has a cylindrical form complementary to the interior of the sleeve 20, the outer diameter of the plug 21 being slightly greater than the inner diameter of the sleeve 20 so that the plug 21 inserted from the rear into the sleeve 20 with its outer surface 25 is at least in slight frictional engagement with the sleeve 20. In the inserted state the plug 21 bears in accordance with FIGS. 2 and 3 with its front plane end face 23 on the plane end flange 39.

According to the invention the plug 21 has a forwardly sealed and rearwardly open axial passage 22, the arrangement and configuration of which will be described in detail hereinafter:

The front end of the passage 22 adjoins an elastic plate 18 which is arranged directly behind the needle passage opening 19 and consists of one piece with the material of the soft-elastic plug 21, the front plane end face 24 of said plate being flush with the front end face 23 of the plug 21. The thickness of the elastic plate 18 is so chosen that after withdrawal of the rear portion 16a of the cannula 16 from the piercing position shown in FIG. 3 the pierced opening automatically closes again due to the resilient properties and the clamping of the elastic plate 18.

The rearwardly open passage 22 thus starts at the rear wall of the elastic plate 18. In the front region 22' the passage 22 has a cylindrical or slightly rearwardly widening cross-section, up to a point clearly behind the front edge of the cannula cone 14 disposed in its final position. In this region the diameter of the passage 22 is slightly less than the outer diameter of the tip of the cannula cone 14 so that in the fitted state of the extension 15 in accordance with FIGS. 2 and 3 the front end of the cannula cone 14 enters in sealing enagement all round into the front end of the passage 22. Thus, in the region of the tip of the cannula cone 14 a sealing region 26 is created between the cannula cone 14 and the plug 21.

Directly behind the sealing region 26 the passage 22 abruptly widens slightly. From this point on rearwardly the passage 22 comprises at its periphery axial vent grooves 28 which can be seen in FIGS. 2, 3, 5 and 6. For example, three such vent grooves 28 are arranged distributed over the periphery.

From the abrupt widening of the cross-section of the passage 22 following the sealing region 26 onwards the passage 22 has a constant cross-section up to its rear end. This cross-section is so dimensioned that at a predetermined distance, not too great, behind the sealing region 26, for example at the level of the upper arrow of the reference numeral 27 in FIGS. 2, 3, the outer wall of the cannula cone 14 comes into clamping engagement with the outer wall of the passage 22. Due to the conical widening of the cannula cone 14 rearwardly the clamping between the cannula cone 14 and the plug 21 thus becomes increasingly greater towards the rear. A clamping region 27 is thus formed, the clamping forces being so dimensioned that the extension 15 is reliably detachable from the cannula cone 14 only under relatively large forces to be applied by hand.

Since the clamping of the material of the plug 21 becomes increasingly stronger rearwardly the vent grooves 28 in accordance with FIG. 5 are increasingly more compressed as apparent from the section of FIG. 6. The grooves 28 must be made deep enough to ensure that even at the rear end of the plug 21 they are not completely pressed together and still leave an axial vent.

In the region of the tip of the cannula cone 14 in the plug 21 a peripheral groove 29 is also provided which in the sealing region 26 ensures a defined but not excessive radial clamping of the material of the plug 21 to the material of the cannula cone 14. Preferably, the tip of the cannula cone 14 extends up to the rear wall of the elastic plate 18 whilst the peripheral groove 29 likewise begins immediately behind the elastic plate 18.

In FIGS. 2 and 3 in dashed line bayonet fastening means 30, 31 are also indicated which for example consist of a pin 30 projecting radially from the sleeve 20 and a bayonet fastener slot 31 merely indicated in the guide sleeve 17. These bayonet fastening means may be constructed similar to those described in DE-C2 30 49 503.

The mode of operation of the blood extraction device described with the aid of FIGS. 1 to 6 is as follows:

In the production works firstly the soft-elastic plug 21 is arranged in frictional fit within the sleeve 20, the elastic plate 18 coming to bear on the end flange 39. Thereafter, the extension 15 thus prefabricated is placed axially onto the cannula cone 14 of the closure cap 12. Due to the axial vent passages 28 when this is done no air inclusions occur which might impair the sealing in the sealing region 26 or the clamping in the clamping region 27. Whereas in the sealing region 26 a complete sealing is achieved with comparatively small radial clamping forces, in the clamping region 27 considerably greater clamping forces are generated between the plug 21 and the cannula cone 14 so that as a result the extension 15 is held reliably on the closure cap 12.

The blood extraction device is now ready for cooperation with the guide sleeve 17 and the cannula 16.

If, by way of exception, the blood extraction device is to be used with a normal cannula the sleeve 20 is gripped by hand and with slight turning and axial pulling withdrawn axially from the cannula cone 14. Thereafter, in accordance with FIG. 8 an ordinary commercial cannula 37 with a conventional conical receiving space 40 at the rear end can be placed on the cannula cone 14.

In accordance with FIG. 7 the passage 22 following the cylindrical region 22' may also have a square form, the corners of the square forming the axial vent grooves between which clamping jaws lie which are formed by the straight sides of the square and are in clamping engagement with the outer periphery of the cannula cone 14.

An essential purpose of the axial vent grooves 28 is also to ensure that when the extension 15 is pulled off axially after a blood extraction no fluid is sucked outwardly from the interior of the cannula cone 14. For because the sealing region 26 is made only very short axially the region 22' of the passage comes into flow connection with the vent grooves 28 even after a slight withdrawal movement of the sleeve 21, thereby avoiding buildup of a partial vacuum in the passage region 22' which would permit sucking up of fluid.

I claim:

1. Blood extraction device comprising an evacuated or evacuatable extraction tube (11) which is open at one end and onto which a closure cap (12) can be detachably fitted which carries a cannula cone (14) which projects forwardly parallel to the tube axis (13) and extends concentrically into an at least substantially cylindrical extension (15) which has a smaller diameter than the extraction tube (11), is constructed as a rearwardly open tube and consists of a rearwardly open stiff sleeve (20) closed at the front except for a needle passage opening (19) and a plug (21) adapted to be fitted sealingly onto the cannula cone (14) and having a passage (22), and onto which a guide sleeve (17) can be pushed axially from the front, said sleeve being mateable therewith, open at the rear and carrying at the front a cannula (16) sharpened on both ends, the cannula end (16a) extending into the interior of the guide sleeve (17) piercing an elastic plate (18) arranged near the needle passage opening (19), in axial alignment therewith and representing a part of the extension (15) and thus establishing a flow connection between the interior of the cannula (16) and the interior of the cannula cone (14), characterized in that the plug is a soft-elastic member which is inserted fittingly into the stiff sleeve (20) and formed of rubber and which has a passage (22) which is open towards the closure cap (12), is adapted to be brought into a clamping fit with the cannula cone (14) holding the extension (15) firmly but releasably on the closure cap (12) and which is sealed at the front by the elastic plate (18), the plug (21) having an outer surface (25) which is pressed against an inner peripheral surface of the sleeve (20) in response to fitting of the extension (15) on the cannula cone (14).

2. Device according to claim 1, characterized in that the elastic plate (18) consists of one piece with the plug (21).

3. Device according to claim 1, characterized in that the front end face (24) of the elastic plate (18) is flush with the front end face (23) of the plug (21).

4. Device according to claim 1, characterized in that the plug (21) has a cylindrical outer surface (25) and the sleeve (20) has a cylindrical inner peripheral surface.

5. Device according to claim 1, characterized in that the plug (21) without inserted cannula cone (14) fits with easy self-retaining frictional fit in the sleeve (20).

6. Device according to claim 1, characterized in that the passage (22) is surrounded in the region of the tip of the cannula cone (14) sealingly by the material of the plug (21) so that a sealing region (26) is present there.

7. Device according to claim 6, characterized in that the passage (22) comprises behind the sealing region (26) at least one axially extending vent groove (28) and in said region (27) is detachably connected in firm clamping fit to the cannula cone (14).

8. Device according to claim 6, characterized in that the sealing region (26) extends over 5 to 20%, in particular about 10%, of the length of the portion of the passage (22) in contact with the cannula cone (14).

9. Device according to claim 1, characterized in that the passage (22) comprises behind the elastic plate (18) a short portion (22') of circular cross-section which has a slightly smaller diameter than the front end region of the cannula cone (14) likewise having a circular cross-section and into which the front end region of the cannula cone (14) sealingly engages.

10. Device according to claim 1, characterized in that the cross-section of the passage (22) widens behind the sealing region (26) but only to such a slight extent that due to the conical widening of the cannula cone (14) a clamping region (27) is still present.

11. Device according to claim 10, characterized in that the cross-section of the passage (22) widens abruptly behind the sealing region (26) and then remains unchanged up to the rear end of the passage (22).

12. Device according to claim 1, characterized in that in the clamping region (27) at least one, preferably however a plurality of circumferentially distributed axial vent grooves (28) are provided of such a depth that even when the extension is fitted on the cannula cone (14) an air passage still remains at the rear end.

13. Device according to claim 1, characterized in that the passage (22) comprises in the clamping region (27) a noncircular preferably square cross-section.

14. Device according to claim 1, characterized in that in the region of the front end of the cannula cone (14) in the outer surface (25) of the plug (22) a peripheral groove (29) is disposed which permits a gentle and uniform resilient widening of the passage (22) on insertion of the tip of the cannula cone (14) in said region and thus a uniform sealing engagement of the plug (22) in the sealing region (26) on the periphery of the cannula cone (14).

15. Device according to claim 1, characterized in that the tip of the cannula cone (14) extends at least approximately up to the rear face of the elastic plate (18).

16. Device according to claim 14, characterized in that the peripheral groove (26) starts immediately behind the region of the elastic plate (18).

17. Device according to claim 1, characterized in that the sleeve (20) and the guide sleeve (17) comprise bayonet fastening means (30, 31).

18. The device according to claim 1 wherein the cannula cone (14) radially presses the outer surface (25) of the plug (21) against the inner peripheral surface of sleeve (20) when the extension (15) is fitted on the cannula cone (14).

19. Blood extraction device comprising an evacuated or evacuatable extraction tube (11) which is open at one end and onto which a closure cap (12) can be detachably fitted which carries a cannula cone (14) which projects forwardly parallel to the tube axis (13) and extends concentrically into an at least substantially cylindrical extension (15) which has a smaller diameter than the extraction tube (11), is constructed as a rearwardly open tube and consists of a rearwardly open stiff sleeve (20) closed at the front except for a needle passage opening (19) and a plug (21) adapted to be fitted sealingly onto the cannula cone (14) and having a passage (22), and onto which a guide sleeve (17) can be pushed axially front the front, said sleeve being mateable therewith, open at the rear and carrying at the front a cannula (16) sharpened on both ends, the cannula end (16a) extending into the interior of the guide sleeve (17) piercing an elastic plate (18) arranged near the needle passage opening (19), in axial alignment therewith and representing a part of the extension (15) and thus establishing a flow connection between the interior of the cannula (16) and the interior of the cannula cone (14), characterized in that the plug is a soft-elastic member having a cylindrical form mateable with an inner peripheral surface of the sleeve (20) along substantially its entire length and which is inserted fittingly into the stiff sleeve (20) and formed of rubber and which has a passage (22) which is open towards the closure cap (12), is adapted to be brought into a clamping fit with the cannula cone (14) holding the extension (15) firmly but releasably on the closure cap (12) and which is sealed at the front by the elastic plate (18).

20. The device according to claim 19 wherein the cannula cone (14) radially presses an outer surface (25) of plug (21) against the inner peripheral surface of sleeve (20) when the extension (15) is fitted on cannula cone (14).

* * * * *